US007745643B2

(12) United States Patent
Cannizzo et al.

(10) Patent No.: US 7,745,643 B2
(45) Date of Patent: Jun. 29, 2010

(54) METHODS OF SYNTHESIZING CYCLIC NITRO COMPOUNDS

(75) Inventors: Louis F. Cannizzo, Ogden, UT (US); Kirstin F. Warner, King George, VA (US); Robert B. Wardle, Logan, UT (US); Stephen P. Velarde, Christiansburg, VA (US)

(73) Assignee: Alliant Techsystems Inc., Minneapolis, MN (US)

( * ) Notice: Subject to any disclaimer, the term of this patent is extended or adjusted under 35 U.S.C. 154(b) by 0 days.

(21) Appl. No.: 12/252,278

(22) Filed: Oct. 15, 2008

(65) Prior Publication Data

US 2009/0093644 A1 Apr. 9, 2009

Related U.S. Application Data

(62) Division of application No. 11/502,810, filed on Aug. 11, 2006, now Pat. No. 7,507,842.

(60) Provisional application No. 60/707,851, filed on Aug. 12, 2005.

(51) Int. Cl.
*C07D 205/04* (2006.01)
(52) U.S. Cl. ..................................................... 548/953
(58) Field of Classification Search .................. 548/953
See application file for complete search history.

(56) References Cited

U.S. PATENT DOCUMENTS

| | | | |
|---|---|---|---|
| 3,845,770 | A | 11/1974 | Theeuwes et al. |
| 3,916,899 | A | 11/1975 | Theeuwes et al. |
| 4,765,539 | A | 8/1988 | Noakes et al. |
| 5,112,598 | A | 5/1992 | Biesalski |
| 5,336,784 | A | 8/1994 | Hiskey et al. |
| 5,556,611 | A | 9/1996 | Biesalski |
| 5,580,988 | A | 12/1996 | Dave |
| 5,698,155 | A | 12/1997 | Grosswald et al. |
| 5,950,619 | A | 9/1999 | van der Linden et al. |
| 5,954,047 | A | 9/1999 | Armer et al. |
| 5,970,974 | A | 10/1999 | Van Der Linden et al. |
| 6,245,799 | B1 | 6/2001 | Asselin et al. |
| 6,407,236 | B1 | 6/2002 | Baraldi et al. |
| 7,163,958 | B2 | 1/2007 | Earl et al. |

FOREIGN PATENT DOCUMENTS

| | | | |
|---|---|---|---|
| WO | 9532715 | A1 | 12/1995 |
| WO | 9916436 | A1 | 4/1999 |
| WO | 9959575 | A1 | 11/1999 |
| WO | 2004032864 | A2 | 4/2004 |
| WO | 2004098538 | A2 | 11/2004 |
| WO | 2004113281 | A1 | 12/2004 |
| WO | 2005046661 | A2 | 5/2005 |
| WO | 2007022121 | A2 | 2/2007 |
| WO | 2007022225 | A2 | 2/2007 |

OTHER PUBLICATIONS

Archibald, T.G., et al., "Synthesis and X-ray Crystal Structure of 1,3,3-Trinitroazetidine," J. Org. Chem, vol. 55, 1990, pp. 2920-2924.
Bamba, Morifere, et al., "Release Mechanisms in Gelforming Sustained Release Preparations," Int. J. Pharm., vol. 2, 1979, pp. 307-315.
Chawla, Garima, et al., "Challenges in Polymorphism of Pharmaceuticals," CRIPS, vol. 5, No. 1, Jan.-Mar. 2004, pp. 9-12.
Dave, Paritosh R., "Acylative Dealkylation of N-tert-Butyl-3-substituted Azetidines: Facile Access to [1.1.0] Azabicyclobutane, 3-Hydroxyazetidinium Hydrochloride, and 3-Azetidinones," J. Org. Chem., vol. 61, 1996, pp. 5453-5455.
During, Matthew J., et al., "Controlled Release of Dopamine from a Polymeric Brain Implant: In Vivo Characterization," Annals of Neurology, vol. 25, No. 4, Apr. 1989, pp. 351-356.
Huguenin, Sandra, et al., "Evaluation of the antitumoral potential of different nitric oxide-donating non-steroidal anti-inflammatory drugs (NO-NSAIDs) on human urological tumor cell lines," Cancer Letters, vol. 218, 2005, pp. 163-170.
Langer, Robert, "New Methods of Drug Delivery," Science, New Series, vol. 249, No. 4976, Sep. 28, 1990, pp. 1527-1533.
Levy, Robert J., "Inhibition of Calcification of Bioprosthetic Heart Valves by Local Controlled-Release Diphosphonate," Science, New Series, vol. 228, No. 4696, Apr. 12, 1985, pp. 190-192.
Naimi, Ebrahim, et al., "Synthesis of 3'- and 5'-Nitrooxy Pyrimidine Nucleoside Nitrate Esters: "Nitric Oxide Donor" Agents for Evaluation as Anticancer and Antiviral Agents," J. Med. Chem., vol. 46, 2003, pp. 995-1004.
Newman, Ann W., et al., "Solid-state analysis of the active pharmaceutical ingredient in drug products," DDT, vol. 8, No. 19, Oct. 2003, pp. 898-905.
Raleigh, R.D., Verschoyle, C., et al., "Pharmacokinetics of Isotretinoin (ISO) in Rats Following Oral Dosing or Aerosol Inhalation," British J. Cancer, vol. 80, Suppl. 2, 96, 1999, p. 269.
Verma, R.K., et al., "Osmotically Controlled Oral Drug Delivery," Drug Dev. Ind. Pharm., vol. 26, No. 7, 2000, pp. 695-708.
Alderman, D.A., "A Review of Cellulose Ethers in Hydrophilic Matrices for Oral Controlled-Release Dosage Forms," Int. J. Pharm. Tech. & Prod. Mfr., vol. 5, No. 3, pp. 1-9, 1984.
Howard, Matthew A., III, et al., "Intracerebral Drug Delivery in Rats with Lesion-Induced Memory Deficits," J. Neurosurg., vol. 71, pp. 105-112, 1989.
Langer, Robert, et al., "Chemical and Physical Structure of Polymers as Carriers for Controlled Release of Bioactive Agents: A Review," JMS—Rev. Macromol. Chem. Phys., Ch. 23, pp. 61-126, 1983.

(Continued)

*Primary Examiner*—Kamal A Saeed
*Assistant Examiner*—Samantha L Shterengarts
(74) *Attorney, Agent, or Firm*—TraskBritt

(57) ABSTRACT

The present invention provides cyclic nitro compounds, pharmaceutical compositions of cyclic nitro compounds and methods of using cyclic nitro compounds and/or pharmaceutical compositions thereof to treat or prevent diseases or disorders characterized by abnormal cell proliferation, such as cancer, inflammation, cardiovascular disease and autoimmune disease.

14 Claims, 8 Drawing Sheets

OTHER PUBLICATIONS

Langer, Robert S., et al., eds., "Medical Applications of Controlled Release," vol. 1, Classes of Systems, Ch. 2, pp. 42-67, CRC Press, Inc., Boca Raton, FL, copyright 1984.

Muehlstaedt et al., caplus an 1976:89768.

Remington, "The Science and Practice of Pharmacy," 19th Edition, vol. II, pp. 1495-1562, 1577-1614, and 1660-1692, Mack Publishing Company, Easton, PA, 1995.

Rosenthal, David I., "A Phase I Single-Dose Trial of Gadolinium Texaphyrin (Gd-Tex), a Tumor Selective Radiation Sensitizer Detectable by Magnetic Resonance Imaging," Clinical Cancer Research, vol. 5, No. 4, pp. 739-745, Apr. 1999.

Sauder, Christopher D., "A Preliminary Trial of the Programmable Implantable Medication System for Insulin Delivery," The New England Journal of Medicine, vol. 321, No. 9, pp. 574-579, Aug. 31, 1989.

Sefton, Michael V., "Implantable Pumps," CRC Crit. Rev. Biomed. Eng., vol. 14, No. 3, pp. 201-237, 1987.

Smolen, Victor F., et al., eds., "Controlled Drug Bioavailability," vol. 1, Drug Product Design and Performance, Ch. 7, pp. 203-237, John Wiley & Sons, New York, NY, copyright 1984.

Treat, Joseph, et al., "Liposome Encapsulated Doxorubicin Preliminary Results of Phase I and Phase II Trials," Liposomes in the Therapy of Infectious Diseases and Cancer, Proceedings of the Ciba-Geigy-Squibb-UCLA Colloquium at Lake Tahoe, CA, Feb. 16-20, 1988, pp. 353-365.

Goodson, J. Max, "Dental Applications," Chapter 6 of Medical Applications of Controlled Release, vol. II, pp. 115-138, CRC Press, Inc., Boca Raton, FL, copyright 1984.

Jia, Q., et al., "NO donors with anticancer activity," Expert Opinion on Therapeutic Patents, vol. 12, No. 6 (2002), pp. 819-826, Great Britain.

Konovalova, N.P., et al., "Nitric oxide donor increases the efficiency of cytostatic therapy and retards the development of drug resistance," Nitric Oxide, vol. 8, No. 1 (Feb. 2003), pp. 59-64.

Ling, C., et al., "Phase I study of CM-Na combined with concurrent radiochemotherapy for advanced esophageal carcinoma (abstract)," Chinese Journal of Cancer, vol. 24, No. 5 (May 2005), (U.S. National Library of Medicine, Bethesda, MD, May 2005).

Sandler, G., "Clinical evaluation of propatylnitrate in angina pectoris," British Medical Journal, vol. 2, No. 5269 (Dec. 30, 1961), pp. 1741-1744.

Stamler, J.S., et al., "Inhaled ethyl nitrite gas for persistent pulmonary hypertension in infants," The Lancet, Lancet Limited, vol. 360, No. 9350 (Dec. 21, 2002), p. 2077, Great Britain.

Electrochemical Oxidation of Alkylnitro Compounds PP-1345, A SERDP 'SEED' Activity, initial submission Jun. 30, 2004; amended Aug. 17, 2004; points of contact Scott K Lusk and Alan N. Green.

METHODS OF SYNTHESIZING CYCLIC NITRO COMPOUNDS

CROSS-REFERENCE TO RELATED APPLICATIONS

This application is a divisional of U.S. patent application Ser. No. 11/502,810, filed Aug. 11, 2006, pending, which application claims priority to U.S. Provisional Application No. 60/707,851, filed Aug. 12, 2005, which is hereby incorporated by reference in its entirety.

FIELD OF THE INVENTION

The present invention relates generally to pharmaceutical compositions of cyclic nitro compounds and methods of using cyclic nitro compounds and pharmaceutical compositions thereof to treat or prevent diseases characterized by abnormal cell proliferation, such as cancer.

BACKGROUND OF THE INVENTION

Abnormal cell proliferation is a characteristic symptom of cancer. Further, abnormal cell proliferation has been implicated in numerous other diseases (e.g., cardiovascular diseases, inflammatory diseases such as rheumatoid arthritis, diabetic retinopathy, etc.). Although many methods for treating or preventing aberrant cell proliferation have been developed, a significant problem with most existing therapies is selectively distinguishing between normal and abnormal cell proliferation.

Radiotherapy is one promising approach to selectively targeting abnormal cell proliferation. A number of different radiosensitizers have been described in the art and include thiols, nitroimidazoles and metal texaphyrin compounds (see, e.g., Rosenthal et al., *Clin. Cancer. Res.*, 1999, 739). Significant problems with existing radiosensitization approaches are (1) the formation of toxic byproducts derived from the radiosensitizers, which has limited their usefulness in cancer therapy; and (2) achieving sufficiently high density of free radicals to be efficacious under dose limiting toxicity.

Another popular approach to selectively targeting abnormal cell proliferation is treatment with bioreductive compounds, which are selectively activated in a reducing environment. Since many cancers typically contain regions of low oxygen tension (i.e., hypoxia), compounds with low redox potentials (i.e., bioreductive compounds) may be selectively activated in the reducing environment of tumor cells without external activation.

Accordingly, new compounds are required to fully explore treating or preventing abnormal cell proliferation. These new compounds may have radiotherapeutic activity or bioreductive activity. Such compounds may be effective in treating or preventing various diseases associated with abnormal cell proliferation, such as cancer, without forming toxic byproducts.

SUMMARY OF THE INVENTION

The present invention satisfies this and other needs by providing cyclic nitro compounds, pharmaceutical compositions of cyclic nitro compounds and methods of using cyclic nitro compounds or pharmaceutical compositions thereof to treat or prevent diseases associated with abnormal cell proliferation.

In a first aspect, a compound of structural Formula (I):

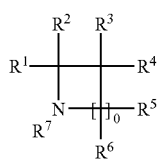

or salts, solvates or hydrates thereof is provided wherein:
$R^1$, $R^2$, $R^3$ and $R^4$ are each independently, hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, halo, hydroxy or nitro;

each $R^5$ and $R^6$ are each independently, hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, halo, hydroxy or nitro;

O is 0, 1, 2, 3 or 4;

$R^7$ is substituted alkyl, substituted arylalkyl, substituted heteroalkyl, substituted heteroaryl, substituted heteroarylalkyl, substituted acyl, substituted alkoxycarbonyl, substituted phosphonyl or substituted sulfonyl;

provided that at least one of $R^1$, $R^2$, $R^3$, $R^4$, $R^5$ and $R^6$ are nitro.

In a second aspect, methods for treating or preventing diseases or disorders characterized by abnormal cell proliferation are provided. The methods generally involve administering to a patient in need of such treatment or prevention a therapeutically effective amount of a cyclic nitro compound or a pharmaceutically acceptable salt, hydrate, solvate or N-oxide thereof.

In a third aspect, pharmaceutical compositions of cyclic nitro compounds are provided. The pharmaceutical compositions generally comprise one or more cyclic nitro compounds, pharmaceutically acceptable salts, hydrates, solvates or N-oxides thereof and a pharmaceutically acceptable vehicle. The choice of vehicle will depend upon, among other factors, the desired mode of administration.

In a fourth aspect, pharmaceutical compositions for treating or preventing diseases or disorders characterized by abnormal cell proliferation are provided. The methods generally involve administering to a patient in need of such treatment or prevention a therapeutically effective amount of a pharmaceutical composition comprising a cyclic nitro compound or a pharmaceutically acceptable salt, hydrate, solvate or N-oxide thereof and a pharmaceutically acceptable vehicle.

DETAILED DESCRIPTION OF THE PREFERRED EMBODIMENTS

Definitions

Figure 1:
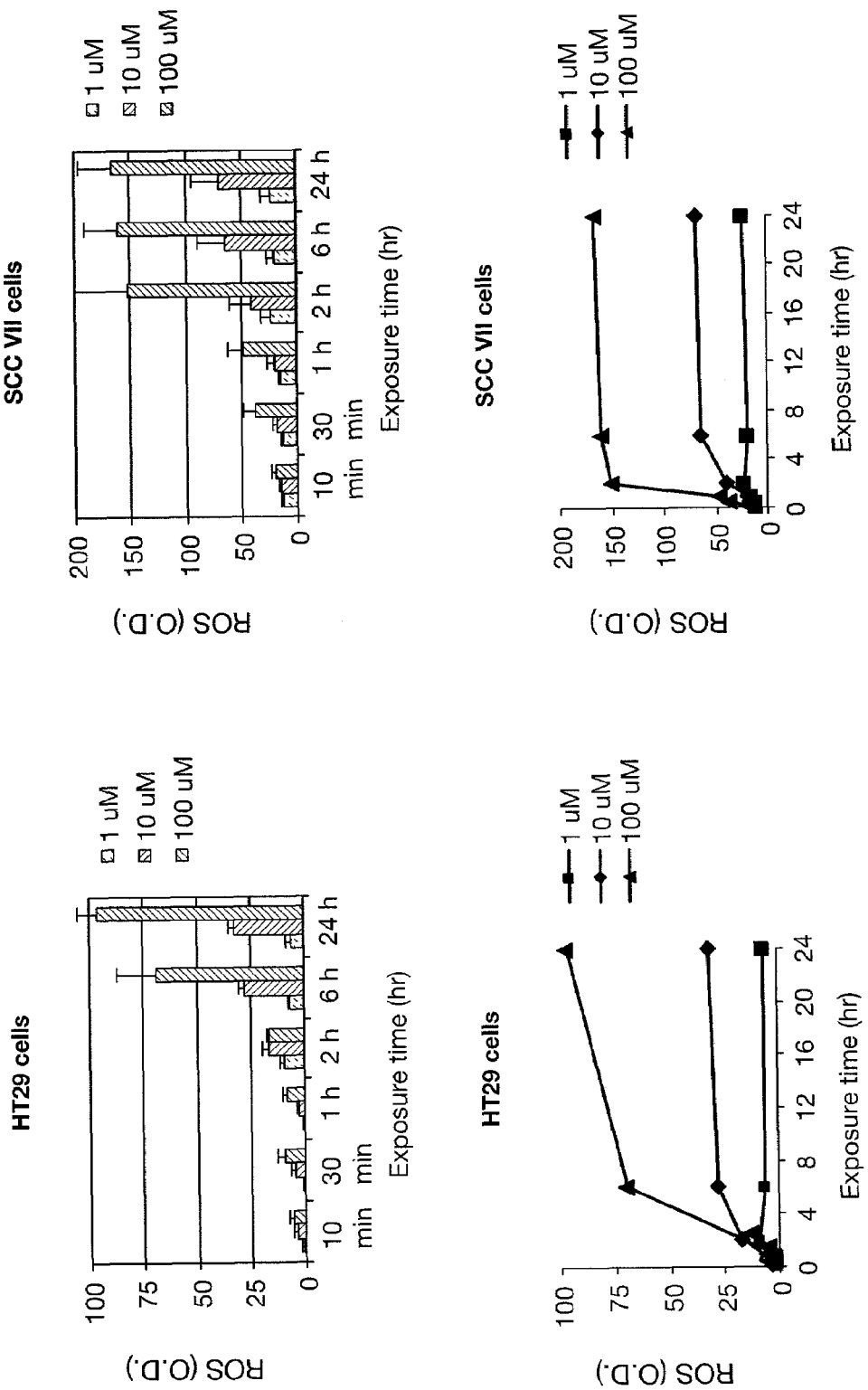
FIG. 1 illustrates the dose and cell line dependency of ROS production in tumor cells in the presence of ABDNAZ.

"Alkyl" by itself or as part of another substituent refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms. In other embodiments, an alkyl group comprises 1 to 10 carbon atoms. In still other embodiments, an alkyl group comprises from 1 to 6 carbon atoms.

"Alkanyl" by itself or as part of another substituent refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl ; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —C(O)R$^{30}$, where R$^{30}$ is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cyclohexylcarbonyl, cyclohexylmethylcarbonyl, benzoyl, benzylcarbonyl, and the like.

"Alkoxycarbonyl" by itself or as part of another substituent refers to a radical —C(O)OR$^{31}$ where R$^{31}$ represents an alkyl or cycloalkyl group as defined herein. Representative examples include, but are not limited to, methoxycarbonyl, ethoxycarbonyl, propoxycarbonyl, butoxycarbonyl, cyclohexyloxycarbonyl and the like.

"Aryl" by itself or as part of another substituent refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, αs-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In some embodiments, an aryl group comprises from 6 to 20 carbon atoms. In other embodiments, an aryl group comprises from between 6 to 12 carbon atoms.

"Arylalkyl" by itself or as part of another substituent refers to an acyclic alkyl group in which one of the hydrogen atoms bonded to a carbon atom, typically a terminal or sp3 carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, naphthobenzyl, 2-naphthophenylethan-1-yl, and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$) and the aryl moiety is ($C_6$-$C_{20}$). In other embodiments, an arylalkyl group is ($C_6$-$C_{20}$) arylalkyl, e.g., the alkanyl, alkenyl or alkynyl moiety of the arylalkyl group is ($C_1$-$C_8$) and the aryl moiety is ($C_6$-$C_{12}$).

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —O—O-13 , —S—S—, —O—S—, —NR$^{34}$R$^{35}$—, =N—N=, N=N—, —N=NR$^{36}$R$^{37}$, —PR$^{38}$—, —P(O)$_2$—, —POR$^{39}$—, —O—P(O)$_2$—, —SO—, —SO$_2$—, —SNR$^{40}$R$^{41}$—, and the like, where R$^{34}$, R$^{35}$, R$^{36}$, R$^{37}$, R$^{38}$, R$^{38}$, R$^{40}$, and R$^{41}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group is between 5-20 membered heteroaryl. In other embodiments, the heteroaryl group is between 5-10 membered heteroaryl. In some embodiments, heteroaryl groups include those derived from thiophene, pyrrole, benzothiophene, benzofuran, indole, pyridine, quinoline, imidazole, oxazole and pyrazine.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl and/or heteroarylalkynyl is used. In some embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20 membered heteroaryl. In other embodiments, the heteroarylalkyl group is a 6-20 membered heteroarylalkyl, e.g., the alkanyl, alkenyl or alkynyl moiety of the heteroarylalkyl is 1-8 membered and the heteroaryl moiety is a 5-12 membered heteroaryl.

"Parent Aromatic Ring System" by itself or as part of another substituent refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, αs-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parent Heteroaromatic Ring System" by itself or as part of another substituent, refers to a parent aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Pharmaceutically acceptable salt" refers to a salt of a cyclic nitro compound, which is pharmaceutically acceptable and possesses the desired pharmacological activity of the parent compound. Such salts include: (1) acid addition salts, formed with inorganic acids such as hydrochloric acid, hydrobromic acid, sulfuric acid, nitric acid, phosphoric acid and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, t-butylacetic acid, lauryl sulfuric acid, gluconic acid, glutamic acid, hydroxynaphthoic acid, salicylic acid, stearic acid, muconic acid and the like or (2) salts formed when an acidic proton present in the parent compound is replaced by an ammonium ion, a metal ion, e.g., an alkali metal ion (e.g., sodium or potassium), an alkaline earth ion (e.g., calcium or magnesium), or an aluminum ion; or coordinates with an organic base such as ethanolamine, diethanolamine, triethanolamine, N-methylglucamine, morpholine, piperidine, dimethylamine, diethylamine, and the like. Also included are salts of amino acids such as arginates and the like, and salts of organic acids like glucurmic or galactunoric acids and the like.

"Pharmaceutically acceptable vehicle" refers to a diluent, adjuvant, excipient or carrier with which a cyclic nitro compound is administered.

"Patient" includes humans and other mammals.

"Phosphonyl" by itself or as part of another substituent refers to a radical —P(O)(OR$^{32}$)$_2$, where each R$^{32}$ is independently hydrogen, alkyl, cycloalkyl, cycloheteroalkyl, aryl, arylalkyl, heteroalkyl, heteroaryl, heteroarylalkyl as defined herein.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Substituted" refers to a group in which one or more hydrogen atoms are independently replaced with the same or different substituent(s). Typical substituents include, but are not limited to, -M, —R$^{60}$, —O$^-$, =O, —OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, —ONO$_2$, =N$_2$, —N$_3$, —S(O)$_2$O$^-$, —S(O)$_2$OH, —S(O)$_2$R$^{60}$, —OS(O$_2$)O$^-$, —OS(O)$_2$R$^{60}$, —P(O)(—)$_2$, —P(O)(OR$^{60}$)(O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O$^-$, —C(S)OR$^{60}$, —NR$^{62}$C(O)NR$^{60}$R$^{61}$, —NR$^{62}$C(S)NR$^{60}$R$^{61}$, —NR$^{62}$C(NR$^{63}$)NR$^{60}$R$^{51}$ and —C(NR$^{62}$)NR$^{60}$R$^{61}$ where M is independently a halogen; R$^{60}$, R$^{61}$, R$^{62}$ and R$^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or, optionally, R$^{60}$ and R$^{61}$, together with the nitrogen atom to which they are bonded, form a cycloheteroalkyl or substituted cycloheteroalkyl ring; and R$^{64}$ and R$^{65}$ are independently hydrogen, alkyl, substituted alkyl, aryl, cycloalkyl, substituted cycloalkyl, cyclohetereoalkyl, substituted cyclohetereoalkyl, aryl, substituted aryl, heteroaryl or substituted heteroaryl, or, optionally, $R^{64}$ and R65 together with the nitrogen atom to which they are bonded, form a cyclohetereoalkyl or substituted cyclohetereoalkyl ring. In some embodiments, substituents include -M, $-R^{60}$, $=O$, $-OR^{60}$, $-SR^{60}$, $-S^-$, $=S$, $-NR^{60}R^{61}$, $=NR^{60}$, $-CF_3$, $-CN$, $-OCN$, $-SCN$, $-NO$, $-NO_2$, $-ONO_2$, $=N_2$, $-N_3$, $-S(O)_2R^{60}$, $-OS(O_2)O^-$, $-OS(O)_2R^{60}$, $-P(O)(O^-)_2$, $-P(O)(OR^{60})(O^-)$, $-OP(O)(OR^{60})(OR^{61})$, $-C(O)R^{60}$, $-C(S)R^{60}$, $-C(O)OR^{60}$, $-C(O)NR^{60}R^{61}$, $-C(O)O^-$, $-NR^{62}C(O)NR^{60}R^{61}$, where $R^{60}$, $R^{61}$ and $R^{62}$ are as defined above. In other embodiments, substituents include $-M$, $-R^{60}$, $=O$, $-OR^{60}$, $-SR^{60}$, $-NR^{60}R^{61}$, $-CF_3$, $-CN$, $-NO_2$, $-ONO_2$, $-S(O)_2R^{60}$, $-P(O)(OR^{60})(O^-)$, $-OP(O)(OR^{60})(OR^{61})$, $-C(O)R60$, $-C(O)OR^{60}$, $-C(O)NR^{60}R^{61}$ and $-C(O)O^-$ where $R^{60}$, $R^{61}$ and $R^{62}$ are as defined above. In still other embodiments, substituents include -M, $-R^{60}$, $=O$, $-OR^{60}$, $-SR^{60}$, $-NR^{60}R^{61}$, $-CF_3$, $-CN$, $-NO_2$, $-ONO_2$, $-S(O)_2R^{60}$, $-OP(O)(OR^{60})(OR^{61})$, $-C(O)R^{60}$, $-C(O)OR^{60}$ and $-C(O)O^-$, where $R^{60}$, $R^{61}$ and $R^{62}$ are as defined above.

"Sulfonyl" by itself or as part of another substituent refers to a radical $-S(O)_2R_{33}$, where each $R^{33}$ is independently hydrogen, alkyl, cycloalkyl, cyclohetereoalkyl, aryl, arylalkyl, heteroalkyl, heteroaryl, heteroarylalkyl as defined herein.

"Treating" or "treatment" of any disease or disorder refers, in one embodiment, to ameliorating the disease or disorder (i.e., arresting or reducing the development of the disease or at least one of the clinical symptoms thereof). In another embodiment, "treating" or "treatment" refers to ameliorating at least one physical parameter, which may not be discernible by the patient. In yet another embodiment, "treating" or "treatment" refers to inhibiting the disease or disorder, either physically, (e.g., stabilization or eradication of a discernible symptom), physiologically, (e.g., stabilization or eradication of a physical parameter) or both. In yet another embodiment, "treating" or "treatment" refers to delaying the onset of the disease or disorder.

"Therapeutically effective amount" means the amount of a compound that, when administered to a patient for treating or preventing a disease, is sufficient to effect such treatment or prevention of the disease. The "therapeutically effective amount" will vary depending on the compound, the disease and its severity and the age, weight, etc., of the patient to be treated.

Reference will now be made in detail to embodiments of the invention. While the invention will be described in conjunction with these embodiments, it will be understood that it is not intended to limit the invention to those preferred embodiments. To the contrary, it is intended to cover alternatives, modifications, and equivalents as may be included within the spirit and scope of the invention as defined by the appended claims.

Cyclic Nitro Compounds and Their Use to Treat or Prevent Abnormal Cell Proliferation The present invention provides cyclic nitro compounds, pharmaceutical compositions of cyclic nitro compounds and methods of using cyclic nitro compounds or pharmaceutical compositions thereof to treat or prevent diseases associated with abnormal cell proliferation.

The methods generally involve administering to a patient in need of such treatment or prevention a therapeutically effective amount of a cyclic nitro compound or a pharmaceutically acceptable salt, hydrate, solvate or N-oxide thereof. In one embodiment, the cyclic nitro compound is intracellularly activated by the reducing environment of a tumor cell. In another embodiment, the patient is irradiated to activate the cyclic nitro compound. Without wishing to be bound by theory, irradiation or reduction of cyclic nitro compounds may lead to formation of free radicals that subsequently prevent cell replication and kill cells, presumably by interfering with DNA replication and/or reacting with cell membranes. However, other mechanisms, presently unknown, may account for the efficacy of cyclic nitro compounds in treating or preventing abnormal cell proliferation.

Accordingly, in some embodiments, the cyclic nitro compounds of the present invention may be activated by both intracellular reduction and external irradiation. In these embodiments, a synergistic or additive effect may be observed.

Cyclic nitro compounds are generally organic compounds substituted with one or more nitro groups (i.e., nitro compounds) but also include nitrate salts (e.g., ammonium dinitride, aluminum trinitride, etc.). Typically, cyclic nitro compounds have a high enthalpy of formation (i.e., decomposition of cyclic nitro compounds releases a high amount of energy). In some embodiments, cyclic nitro compounds have an enthalpy of formation that varies between about 5 kcal/mole and about 150 kcal/mole, more preferably, between about 10 kcal/mole and about 110 kcal/mole. The enthalpy of formation of nitro compounds may be readily calculated by methods known to the skilled artisan. Accordingly, cyclic nitro compounds include those nitro compounds that decompose with explosive force upon activation. Such compounds may be readily identified by those of skill in the art by calculation of the enthalpy of formation.

Cyclic nitro compounds may also be reduced at low reduction potentials. Cyclic voltammetry demonstrates that electron transfer to cyclic nitro compounds occurs between about —0.1 volts and about—1.0 volts using standard electrodes (e.g., mercury or carbon cathode and platinum anode) and electrolyte solutions.

In some embodiments, cyclic nitro compounds contain a high density of nitro groups (i.e., the nitro groups represent a significant fraction of the overall mass of the compound). In other embodiments, cyclic nitro compounds contain two nitro groups. In still other embodiments, cyclic nitro compounds contain three nitro groups. In still other embodiments, cyclic nitro compounds contain three or more nitro groups. In still other embodiments, a cyclic nitro compound contains six nitro groups.

In some embodiments, the cyclic nitro compound is a nitrocarbon which has a ratio of nitro groups to carbon atoms of 1:1. In other embodiments, the cyclic nitro compound is a nitrocarbon which has a ratio of nitro groups to carbon atoms of 1:2.

In some embodiments, a compound of structural Formula (I):

or salts, solvates or hydrates thereof is provided wherein:

$R^1$, $R^2$, $R^3$ and $R^4$ are each independently, hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, halo, hydroxy or nitro;

each $R^5$ and $R^6$ are each independently, hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, halo, hydroxy or nitro;

O is 0, 1, 2, 3 or 4;

R7 is substituted alkyl, substituted arylalkyl, substituted heteroalkyl, substituted heteroaryl, substituted heteroarylalkyl, substituted acyl, substituted alkoxycarbonyl, substituted phosphonyl or substituted sulfonyl;

provided that at least one of $R^1$, $R^2$, $R^3$, $R^4$, $R^5$ and $R^6$ are nitro.

In some embodiments, at least two of $R^1$, $R^2$, $R^3$, $R^4$, $R^5$ or $R^6$ are nitro. In other embodiments, $R^1$, $R^2$, $R^3$ and $R^4$ are each independently, hydrogen, alkyl or nitro and each $R^5$ and $R^6$ are each independently, hydrogen, alkyl or nitro. In still other embodiments, $R^7$ is substituted alkyl, substituted acyl, substituted alkoxycarbonyl, substituted phosphonyl or substituted sulfonyl. In still other embodiments, $R^7$ is alkyl, acyl, alkoxycarbonyl, phosphonyl or sulfonyl substituted with one or more halogen, —$CF_3$ or —$OS(O)_2R^8$, wherein $R^8$ is alkyl, substituted alkyl, aryl or substituted aryl. In still other embodiments, $R^3$ and $R^4$ are nitro.

In some embodiments, $R^1$, $R^2$, $R^3$ and $R^4$ are each independently, hydrogen, alkyl or nitro, each $R^5$ and $R^6$ are each independently, hydrogen, alkyl or nitro and $R^7$ is substituted alkyl, substituted acyl, substituted alkoxycarbonyl, substituted phosphonyl or substituted sulfonyl. In other embodiments, $R^1$, $R^2$, $R^3$ and $R^4$ are each independently, hydrogen, alkyl or nitro, each $R^5$ and $R^6$ are each independently, hydrogen, alkyl or nitro and $R^7$ is alkyl, acyl, alkoxycarbonyl, phosphonyl or sulfonyl substituted with one or more halogen, —$CF_3$ or —$OS(O)_2R^8$, wherein $R^8$ is alkyl, substituted alkyl, aryl or substituted aryl. In still other embodiments, $R^1$ and $R^2$ are each independently, hydrogen, alkyl or nitro, $R^3$ and $R^4$ are nitro, each $R^5$ and $R^6$ are each independently, hydrogen, alkyl or nitro, $R^7$ is substituted alkyl, substituted acyl, substituted alkoxycarbonyl, substituted phosphonyl or substituted sulfonyl. In still other embodiments, $R^1$ and $R^2$ are each independently, hydrogen, alkyl or nitro, $R^3$ and $R^4$ are nitro, each $R^5$ and $R^6$ are each independently, hydrogen, alkyl or nitro, $R^7$ is alkyl, acyl, alkoxycarbonyl, phosphonyl or sulfonyl substituted with one or more halogen, —$CF_3$ or —$OS(O)_2R^8$, wherein $R^8$ is alkyl, substituted alkyl, aryl or substituted aryl. In some of any of the above embodiments, O is 1.

In some embodiments, $R^1$ and $R^2$ are each independently, hydrogen, alkyl or nitro, $R^3$ and $R^4$ are nitro, $R^5$ and $R^6$ are each independently, hydrogen, alkyl or nitro, $R^7$ is alkyl or acyl substituted with one or more halogens or —$CF_3$ and O is 1. In other embodiments, $R^1$ and $R^2$ are hydrogen, $R^3$ and $R^4$ are nitro, $R^5$ and $R^6$ are hydrogen, $R^7$ is alkyl or acyl substituted with one or more halogen or —$CF_3$ and O is 1.

In some embodiments, the cyclic nitro compound has the structure:

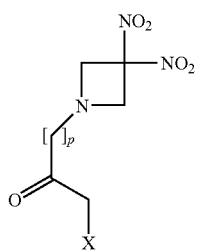 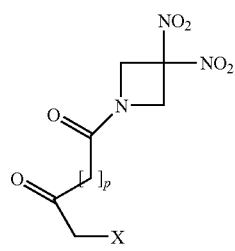

wherein each X is independently —F, —Cl, —Br, —I or —$OS(O)_2R^8$ where $R^8$ is methyl, $CF_3$, phenyl or tolyl and each p is independently 1, 2, 3, or 4.

In other embodiments, the cyclic nitro compound has the structure:

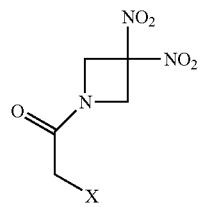

wherein each X is independently —F, —Cl, —Br, —I, —$OS(O)_2R^8$ where $R^8$ is methyl, $CF_3$, phenyl or tolyl. In some specific embodiments, the cyclic nitro compound has the structure:

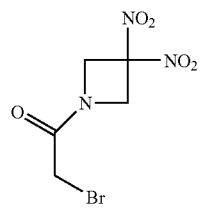

commonly referred to as ABDNAZ.

Cyclic nitro compounds may exist in several tautomeric forms and mixtures thereof. Cyclic nitro compounds may also include isotopically labeled compounds where one or more atoms have an atomic mass different from the atomic mass conventionally found in nature. Examples of isotopes that may be incorporated into cyclic nitro compounds include, but are not limited to, $^2H$, $^3H$, $^{13}C$, $^{14}C$, $^{15}N$, $^{18}O$ and $^{17}O$. Cyclic nitro compounds may exist in unsolvated forms as well as solvated forms, including hydrated forms or N-oxides. In general, hydrated and solvated forms are within the scope of the present invention. Certain cyclic nitro compounds may exist in multiple crystalline or amorphous forms. In general, all physical forms are equivalent for the uses contemplated by the present invention and are intended to be within the scope of the present invention.

Cyclic nitro compounds may be activated by intracellular reduction. In some embodiments, cyclic nitro compounds are activated by intracellular reduction in hypoxic tumor cells, secondary to elevated glutathione levels (high GSH:GSSG (i.e., glutathione to glutathione disulfide ratios)) and possibly high levels of other antioxidant enzymes in many tumor cells and/or a median tumor cell $pO^2$ of less than about 10 mm Hg.

Cyclic nitro compounds may also be activated by application of external energy. Methods useful for decomposing cyclic nitro compounds include, but are not limited to, irradiation (e.g., with x-rays, visible light, infrared irradiation) ultrasound (e.g., focused ultrasound), electrochemical reduction, heating, co-administration of free radical initiators (e.g., thiols), etc. In some embodiments, a cyclic nitro compound is activated by photon irradiation of the patient. In some embodiments, the patient's tumor is irradiated using a linear accelerator at a dose rate of about 100 cGy/min. The patient may also be treated with electron beam therapy, interoperative radiation therapy, stereostatic radiosurgery and high or low dose brachytherapy.

In some situations the entire patient may be irradiated. In some embodiments, a portion of the patient is irradiated so that only cyclic nitro compound localized in the irradiated portion (e.g., tumor region) of the patient is activated. Preferably, the portion of the patient which is irradiated is the site of abnormal cell proliferation.

Cyclic nitro compounds may be obtained via conventional synthetic methods described in the art or are commercially available, e.g., from ATK Thiokol, Salt Lake City, Utah. Starting materials useful for preparing cyclic nitro compounds and intermediates thereof are commercially available or can be prepared by well-known synthetic methods. Other methods for synthesis of the cyclic nitro compounds described herein and/or starting materials are either described in the art or will be readily apparent to the skilled artisan.

In accordance with the invention, a cyclic nitro compound or a pharmaceutical composition thereof is administered to a patient, preferably a human, suffering from a disease characterized by abnormal cell proliferation. The cyclic nitro compound and pharmaceutical compositions thereof may be used to treat or prevent diseases characterized by abnormal cell proliferation.

Diseases characterized by abnormal cell proliferation include, but are not limited to, cancer (e.g., any vascularized tumor, preferably, a solid tumor, including but not limited to, carcinomas of the lung, breast, ovary, stomach, pancreas, larynx, esophagus, testes, liver, parotid, biliary tract, colon, rectum, cervix, uterus, endometrium, kidney, bladder, prostrate, thyroid, squamous cell carcinomas, adenocarcinomas, small cell carcinomas, melanomas, gliomas, neuroblastomas, sarcomas (e.g., angiosarcomas, chondrosarcomas), diabetes, cardiovascular diseases (e.g., arteriosclerosis), inflammatory diseases (e.g., arthritis, diabetic retinopathy, rheumatoid arthritis, neovascular glaucoma and psoriasis) and autoimmune diseases.

In other embodiments, cyclic nitro compounds may be used for in-vitro sterilization. Biological solutions may be treated with cyclic nitro compounds, which are toxic to pathogenic bacteria, viruses and cells. This process can also be catalyzed by the application of external energy such as light and heat.

Further, in certain embodiments, a cyclic nitro compound and/or pharmaceutical compositions thereof are administered to a patient, preferably a human, as a preventative measure against various diseases or disorders characterized by abnormal cell proliferation. Thus, cyclic nitro compounds and/or pharmaceutical compositions thereof may be administered as a preventative measure to a patient having a predisposition for a disease characterized by abnormal cell proliferation. Accordingly, cyclic nitro compounds and/or pharmaceutical compositions thereof may be used for the prevention of one disease or disorder and concurrently treating another (e.g., preventing arthritis while treating cancer).

Therapeutic/Prophylactic Administration

Cyclic nitro compounds and/or pharmaceutical compositions thereof may be advantageously used in human medicine. As previously described hereinabove, cyclic nitro compounds and/or pharmaceutical compositions thereof are useful for the treatment or prevention of various diseases or disorders such as those listed above.

When used to treat or prevent the above disease or disorders, cyclic nitro compounds and/or pharmaceutical compositions thereof may be administered or applied singly, or in combination with other agents. Cyclic nitro compounds and/or pharmaceutical compositions thereof may also be administered or applied singly, or in combination with other pharmaceutically active agents (e.g., other anti-cancer agents, other arthritis agents, etc.), including other cyclic nitro compounds and/or pharmaceutical compositions thereof.

The current invention provides methods of treatment and prophylaxis by administration to a patient of a therapeutically effective amount of a cyclic nitro compound and/or pharmaceutical composition thereof. The patient is preferably, a mammal and most preferably, is a human.

Cyclic nitro compounds and/or pharmaceutical compositions thereof may be administered orally. Cyclic nitro compounds and/or pharmaceutical compositions thereof may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer a cyclic nitro compound and/or pharmaceutical composition thereof. Methods of administration include, but are not limited to, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes or skin. The mode of administration is left to the discretion of the practitioner, and will depend in-part upon the site of the medical condition. In most instances, administration will result in the release of cyclic nitro compounds and/or pharmaceutical compositions thereof into the bloodstream.

In specific embodiments, it may be desirable to administer one or more cyclic nitro compounds and/or pharmaceutical compositions thereof locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, the implant being of a porous, non-porous, or gelatinous material, including membranes, such as SILASTIC® membranes or fibers. In one embodiment, administration can be by direct injection at the site (or former site) of the disease or disorder.

In certain embodiments, it may be desirable to introduce one or more cyclic nitro compounds and/or pharmaceutical compositions thereof into the central nervous system by any suitable route, including intraventricular, intrathecal and epidural injection. Intraventricular injection may be facilitated by an intraventricular catheter, for example, attached to a reservoir, such as an Ommaya reservoir.

Cyclic nitro compounds and/or pharmaceutical compositions thereof may also be administered directly to the lung by inhalation. For administration by inhalation, cyclic nitro compounds and/or pharmaceutical compositions thereof may be conveniently delivered to the lung by a number of different devices. For example, a Metered Dose Inhaler ("MDI"), which utilizes canisters that contain a suitable low boiling propellant, (e.g., dichlorodifluoromethane, trichlorofluoromethane, dichlorotetrafluoroethane, carbon dioxide or any other suitable gas) may be used to deliver cyclic nitro compounds and/or pharmaceutical compositions thereof directly to the lung.

Alternatively, a Dry Powder Inhaler ("DPI") device may be used to administer a cyclic nitro compound and/or pharmaceutical composition thereof to the lung. DPI devices typically use a mechanism such as a burst of gas to create a cloud of dry powder inside a container, which may then be inhaled by the patient and are well known in the art. A popular variation is the multiple dose DPI ("MDDPI") system, which allows for the delivery of more than one therapeutic dose. MDDPI devices are commercially available from a number of pharmaceutical companies (e.g. Schering Plough, Madison, N.J.). For example, capsules and cartridges of gelatin for use in an inhaler or insufflator may be formulated containing a powder mix of a cyclic nitro compound and/or pharmaceutical composition thereof and a suitable powder base such as lactose or starch for these systems.

Another type of device that may be used to deliver a cyclic nitro compound and/or pharmaceutical composition thereof to the lung is a liquid spray device supplied, for example, by Aradigm Corporation, Hayward, Calif. Liquid spray systems use extremely small nozzle holes to aerosolize liquid drug formulations that may then be directly inhaled into the lung.

In some embodiments, a nebulizer is used to deliver a cyclic nitro compound and/or pharmaceutical composition thereof to the lung. Nebulizers create aerosols from liquid drug formulations by using, for example, ultrasonic energy to form fine particles that may be readily inhaled (see, e.g., Verschoyle et al., *British J. Cancer,* 1999, 80, Suppl. 2, 96). Examples of nebulizers include devices supplied by Sheffield Pharmaceuticals, St. Louis, Mo. (Armer et al., U.S. Pat. No. 5,954,047; van der Linden et al., U.S. Pat. No. 5,950,619; van der Linden et al., U.S. Pat. No. 5,970,974), and Batelle Pulmonary Therapeutics, Columbus, Ohio.

In other embodiments, an electrohydrodynamic ("EHD") aerosol device is used to deliver a cyclic nitro compound and/or pharmaceutical composition thereof to the lung of a patient. EHD aerosol devices use electrical energy to aerosolize liquid drug solutions or suspensions (see, e.g., Noakes et al., U.S. Pat. No. 4,765,539). The electrochemical properties of the formulation may be important parameters to optimize when delivering a cyclic nitro compound and/or pharmaceutical composition thereof to the lung with an EHD aerosol device and such optimization is routinely performed by one of skill in the art. EHD aerosol devices may more efficiently deliver drugs to the lung than existing pulmonary delivery technologies.

In some embodiments, a cyclic nitro compound and/or pharmaceutical compositions thereof can be delivered in a vesicle, in particular a liposome (e.g., Langer, 1990, *Science,* 249:1527-1533; Treat et al., in "Liposomes in the Therapy of Infectious Disease and Cancer," Lopez-Berestein and Fidler (eds.), Liss, N.Y., pp. 353-365 (1989)).

In some embodiments, a cyclic nitro compound and/or pharmaceutical compositions thereof can be delivered via sustained release systems, preferably oral sustained release systems. In other embodiments, a pump may be used (e.g., Langer, supra, Sefton, 1987, *CRC Crit. Ref. Biomed. Eng.* 14:201; Saudek et al., 1989, *N. Engl. J. Med.* 321:574).

In some embodiments, polymeric materials can be used (e.g., "Medical Applications of Controlled Release," Langer and Wise (eds.), CRC Press, Boca Raton, Fla. (1974); "Controlled Drug Bioavailability," Drug Product Design and Performance, Smolen and Ball (eds.), Wiley, N.Y. (1984); Ranger et al., 1983, *J. Macromol. Sci. Rev. Macromol. Chem.* 23:61; Levy et al., 1985, *Science* 228:190; During et al., 1989, *Ann. Neurol.* 25:351; Howard et al., 1989, *J. Neurosurg.* 71:105).

In other embodiments, polymeric materials are used for oral sustained release delivery. Polymers include, but are not limited to, sodium carboxymethylcellulose, hydroxypropylcellulose, hydroxypropylmethylcellulose and hydroxyethylcellulose (most preferred, hydroxypropyl methylcellulose). Other cellulose ethers have been described (Alderman, *Int. J. Pharm. Tech. & Prod. Mfr.* 1984, 5(3) 1-9). Factors affecting drug release are well known to the skilled artisan and have been described in the art (Bamba et al., *Int. J. Pharm.* 1979, 2, 307).

In other embodiments, enteric-coated preparations can be used for oral sustained release administration. Coating materials include polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In other embodiments, osmotic delivery systems are used for oral sustained release administration (Verma et al., *Drug Dev. Ind. Pharm.,* 2000, 26:695-708). In some embodiments, OROS® osmotic devices are used for oral sustained release delivery devices (Theeuwes et al., U.S. Pat. No. 3,845,770; Theeuwes et al., U.S. Pat. No. 3,916,899).

In yet other embodiments, a controlled-release system can be placed in proximity of the target of the cyclic nitro compound and/or pharmaceutical composition, thus requiring only a fraction of the systemic dose (e.g., Goodson, in "Medical Applications of Controlled Release," supra, vol. 2, pp. 115-138 (1984)). Other controlled-release systems previously may also be used (Langer, 1990, *Science* 249:1527-1533).

Pharmaceutical Compositions

The present pharmaceutical compositions typically contain a therapeutically effective amount of one or more cyclic nitro compounds, preferably, in purified form, together with a suitable amount of a pharmaceutically acceptable vehicle, so as to provide the form for proper administration to a patient. When administered to a patient, the cyclic nitro compound and pharmaceutically acceptable vehicles are preferably sterile. Water is a preferred vehicle when the cyclic nitro compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The present pharmaceutical compositions, if desired, can also contain minor amounts of wetting or emulsifying agents, or pH buffering agents. In addition, auxiliary, stabilizing, thickening, lubricating and coloring agents may be used.

Pharmaceutical compositions comprising a cyclic nitro compound may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds into preparations which can be used pharmaceutically. Proper formulation is dependent upon the route of administration chosen.

The present pharmaceutical compositions can take the form of solutions, suspensions, emulsions, tablets, pills, pellets, capsules, capsules containing liquids, powders, sustained-release formulations, suppositories, aerosols, sprays, or any other form suitable for use. In one embodiment, the pharmaceutically acceptable vehicle is a capsule (e.g., Grosswald et al., U.S. Pat. No. 5,698,155). A general discussion of the preparation of pharmaceutical compositions may be found in Remington, "The Science and Practice of Pharmacy," 19$^{th}$ Edition.

For topical administration, a cyclic nitro compound may be formulated as solutions, gels, ointments, creams, suspensions, etc., as is well known in the art.

Systemic formulations include those designed for administration by injection, e.g., subcutaneous, intravenous, intramuscular, intrathecal or intraperitoneal injection, as well as those designed for transdermal, transmucosal, oral or pulmonary administration. Systemic formulations may be made in combination with a further active agent that improves mucociliary clearance of airway mucus or reduces mucous viscosity. These active agents include, but are not limited to, sodium channel blockers, antibiotics, N-acetyl cysteine, homocysteine and phospholipids.

In a preferred embodiment, cyclic nitro compounds are formulated in accordance with routine procedures as a pharmaceutical composition adapted for intravenous administration to human beings. Typically, cyclic nitro compounds are solutions in sterile isotonic aqueous buffer for intravenous administration. For injection, cyclic nitro compounds may be formulated in aqueous solutions, preferably in physiologically compatible buffers such as Hanks' solution, Ringer's solution, or physiological saline buffer. The solution may contain formulatory agents such as suspending, stabilizing and/or dispersing agents. When necessary, the pharmaceutical compositions may also include a solubilizing agent. Pharmaceutical compositions for intravenous administration may optionally include a local anesthetic such as lignocaine to ease pain at the site of the injection. Generally, the ingredients are supplied either separately or mixed together in unit dosage form, for example, as a lyophilized powder or water free concentrate in a hermetically sealed container such as an ampoule or sachette indicating the quantity of active agent. When the cyclic nitro compounds are administered by infusion, the cyclic nitro compounds can be dispensed, for example, with an infusion bottle containing sterile pharmaceutical grade water or saline. When the cyclic nitro compound is administered by injection, an ampoule of sterile water for injection or saline can be provided so that the ingredients may be mixed prior to administration.

For transmucosal administration, penetrants appropriate to the barrier to be permeated are used in the formulation. Such penetrants are generally known in the art.

Pharmaceutical compositions for oral delivery may be in the form of tablets, lozenges, aqueous or oily suspensions, granules, powders, emulsions, capsules, syrups, or elixirs, for example. Orally administered pharmaceutical compositions may contain one or more optional agents, for example, sweetening agents such as fructose, aspartame or saccharin; flavoring agents such as peppermint, oil of wintergreen, or cherry coloring agents and preserving agents, to provide a pharmaceutically palatable preparation. Moreover, when in tablet or pill form, the pharmaceutical compositions may be coated to delay disintegration and absorption in the gastrointestinal tract, thereby providing a sustained action over an extended period of time. Selectively permeable membranes surrounding an osmotically active driving compound are also suitable for orally administered compounds. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5.0 mM to about 50.0 mM), etc. Additionally, flavoring agents, preservatives, coloring agents, bile salts, acylcarnitines, and the like, may be added.

For buccal administration, the pharmaceutical compositions may take the form of tablets, lozenges, etc., formulated in conventional manner.

Liquid drug formulations suitable for use with nebulizers and liquid spray devices and EHD aerosol devices typically include a cyclic nitro compound with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds. Preferably, this material is liquid such as an alcohol, glycol, polyglycol or a fatty acid. Other methods of formulating liquid drug solutions or suspensions suitable for use in aerosol devices are known to those of skill in the art (see, e.g., Biesalski, U.S. Pat. No. 5,112,598; Biesalski, U.S. Pat. No. 5,556,611).

A cyclic nitro compound may also be formulated in rectal or vaginal pharmaceutical compositions such as suppositories or retention enemas, e.g., containing conventional suppository bases such as cocoa butter or other glycerides.

In addition to the formulations described previously, a cyclic nitro compound may also be formulated as a depot preparation. Such long acting formulations may be administered by implantation (for example, subcutaneously or intramuscularly) or by intramuscular injection. Thus, for example, a cyclic nitro compound may be formulated with suitable polymeric or hydrophobic materials (e.g., as an emulsion in an acceptable oil) or ion exchange resins, or as sparingly soluble derivatives, such as a sparingly soluble salt.

When a cyclic nitro compound is acidic or basic, it may be included in any of the above-described formulations as the free acid or free base, a pharmaceutically acceptable salt, a solvate or hydrate. Pharmaceutically acceptable salts substantially retain the activity of the free acid or base, may be prepared by reaction with bases or acids and tend to be more soluble in aqueous and other protic solvents than the corresponding free acid or base form.

Doses

A cyclic nitro compound and/or pharmaceutical composition thereof will generally be used in an amount effective to achieve the intended purpose. For the use to treat or prevent the above diseases or disorders, the cyclic nitro compound and/or pharmaceutical compositions thereof are administered or applied in a therapeutically effective amount.

The amount of a cyclic nitro compound and/or pharmaceutical composition thereof that will be effective in the treatment of a particular disorder or condition disclosed herein will depend on the nature of the disorder or condition, and can be determined by standard clinical techniques known in the art. In addition, in vitro or in vivo assays may optionally be employed to help identify optimal dosage ranges. The amount of a cyclic nitro compound and/or pharmaceutical composition thereof administered will, of course, be dependent on, among other factors, the subject being treated, the weight of the subject, the severity of the affliction, the manner of administration and the judgment of the prescribing physician.

For example, the dosage may be delivered in a pharmaceutical composition by a single administration, by multiple applications or controlled release. Dosing may be repeated intermittently, may be provided alone or in combination with other drugs and may continue as long as required for effective treatment of the disease state or disorder.

Suitable dosage ranges for oral administration are dependent on the efficiency of radiosensitization, but are generally about 0.001 mg to about 100 mg of the cyclic nitro compound per kg body weight. Dosage ranges may be readily determined by methods known to the artisan of ordinary skill.

Suitable dosage ranges for intravenous (i.v.) administration are about 0.01 mg to about 100 mg per kg/ body weight. Suitable dosage ranges for intranasal administration are generally about 0.01 mg/kg body weight to about 1 mg/kg body weight. Suppositories generally contain about 0.01 milligram to about 50 milligrams of a cyclic nitro compound per kg/ body weight and comprise active ingredient in the range of about 0.5% to about 10% by weight. Recommended dosages for intradermal, intramuscular, intraperitoneal, subcutaneous, epidural, sublingual or intracerebral administration are in the range of about 0.001 mg to about 200 mg per kg body weight. Effective doses may be extrapolated from dose-response curves derived from in vitro or animal model test systems. Such animal models and test systems are well known in the art.

The cyclic nitro compounds are preferably assayed in vitro and in vivo, for the desired therapeutic or prophylactic activity, prior to use in humans. For example, in vitro assays can be used to determine whether administration of a specific cyclic nitro compound or a combination of cyclic nitro compounds is preferred. The cyclic nitro compound may also be demonstrated to be effective and safe using animal model test systems.

Preferably, a therapeutically effective dose of a cyclic nitro compound and/or pharmaceutical composition thereof described herein will provide therapeutic benefit without causing substantial toxicity. Toxicity of cyclic nitro compounds and/or pharmaceutical compositions thereof may be determined using standard pharmaceutical procedures and may be readily ascertained by the skilled artisan. The dose ratio between toxic and therapeutic effect is the therapeutic index. A cyclic nitro compound and/or pharmaceutical composition thereof will preferably exhibit particularly high therapeutic indices in treating disease and disorders characterized by aberrant abnormal cell proliferation. The dosage of a cyclic nitro compound and/or pharmaceutical composition thereof described herein will preferably be within a range of circulating concentrations that include an effective dose with little or no toxicity.

Combination Therapy

In certain embodiments of the present invention, cyclic nitro compounds and/or pharmaceutical compositions thereof can be used in combination therapy with at least one other therapeutic agent. The cyclic nitro compound and/or pharmaceutical composition thereof and the therapeutic agent can act additively or, more preferably, synergistically. In one embodiment, a cyclic nitro compound and/or a pharmaceutical composition thereof is administered concurrently with the administration of another therapeutic agent. In another embodiment, a cyclic nitro compound and/or pharmaceutical composition thereof is administered prior or subsequent to administration of another therapeutic agent.

In particular, in one embodiment, cyclic nitro compounds and/or pharmaceutical compositions thereof can be used in combination therapy with other chemotherapeutic agents (e.g., alkylating agents (e.g., nitrogen mustards (e.g., cyclophosphamide, ifosfamide, mechlorethamine, melphalen, chlorambucil, hexamethylmelamine, thiotepa), alkyl sulfonates (e.g., busulfan), nitrosoureas, triazines)), antimetabolites (e.g., folic acid analogs, pyrimidine analogs (e.g., fluorouracil, floxuridine, cytosine arabinoside, etc.)), purine analogs (e.g., mercaptopurine, thioguanine, pentostatin, etc.), natural products (e.g., vinblastine, vincristine, etoposide, tertiposide, dactinomycin, daunorubicin, doxorubicin, bleomycin, mithromycin, mitomycin C, L-asparaginase, interferon alpha), platinum coordination complexes (e.g., cis-platinum, carboplatin, etc.), apoptosis-inducing agents, glutathione-depleting agents or other agents that can alter the redox status of the cell. Those of skill in the art will appreciate that cyclic nitro compounds may also be used in concurrent combination therapy with both the chemotherapeutic agents listed above and radiotherapy.

Therapeutic Kits

The current invention also provides therapeutic kits comprising cyclic nitro compounds and/or pharmaceutical compositions thereof. The therapeutic kits may also contain other compounds (e.g., chemotherapeutic agents, natural products, apoptosis-inducing agents, etc.) or pharmaceutical compositions thereof.

Therapeutic kits may have a single container which contains a cyclic nitro compound and/or pharmaceutical compositions thereof with or without other components (e.g., other compounds or pharmaceutical compositions of these other compounds) or may have a distinct container for each component. Preferably, therapeutic kits include a cyclic nitro compound and/or a pharmaceutical composition thereof packaged for use in combination with the co-administration of a second compound (preferably, a chemotherapeutic agent, a natural product, an apoptosis-inducing agent, etc.) or a pharmaceutical composition thereof. The components of the kit may be pre-complexed or each component may be in a separate distinct container prior to administration to a patient.

The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid.

Preferably, a therapeutic kit will contain apparatus (e.g., one or more needles, syringes, eye droppers, pipette, etc.), which enables administration of the components of the kit.

EXAMPLES

The invention is further defined by reference to the following examples, which describe in detail, preparation of compounds and methods for assaying for biological activity. It will be apparent to those skilled in the art that many modifications, both to materials and methods, may be practiced without departing from the scope.

Example 1

Production of ROS In Tumor

Cells By ABDNAZ And Irradiation

Human colon cancer cell line HT29 cells and murine squamous cell carcinoma cell line SCC VII cells were grown in 96-well plates overnight at 37° C. and then a fluorescent probe 2'7'-dichlorofluorescin diacetate (DCFH-DA) was added at a concentration of 20 µM for 1 hour and then washed out. ABDNAZ was added in the growth media at concentrations of 1 µM, 10 µM or 100 µM. The green fluorescence was observed under a fluorescence microscope and measured using a microplate spectrofluorometer with an excitation at 488 nm and an emission at 525 nm. For cells that were treated with both ABDNAZ and irradiation, the plates were irradiated immediately after addition of ABDNAZ using a $^{137}$Cs source.

FIG. 1 shows the production of reactive oxygen species (ROS) in HT29 cells and SCC VII cells after exposure to ABDNAZ. The production of ROS was dose, time and cell line dependent. The ROS production in HT29 cells was gradually increased over time and peaked at 24 hours. For SCC VII cells, the production of ROS peaked 2 hours after addition of ABDNAZ, and the levels of ROS were significantly higher than that induced in HT29 cells.

Figure 2:
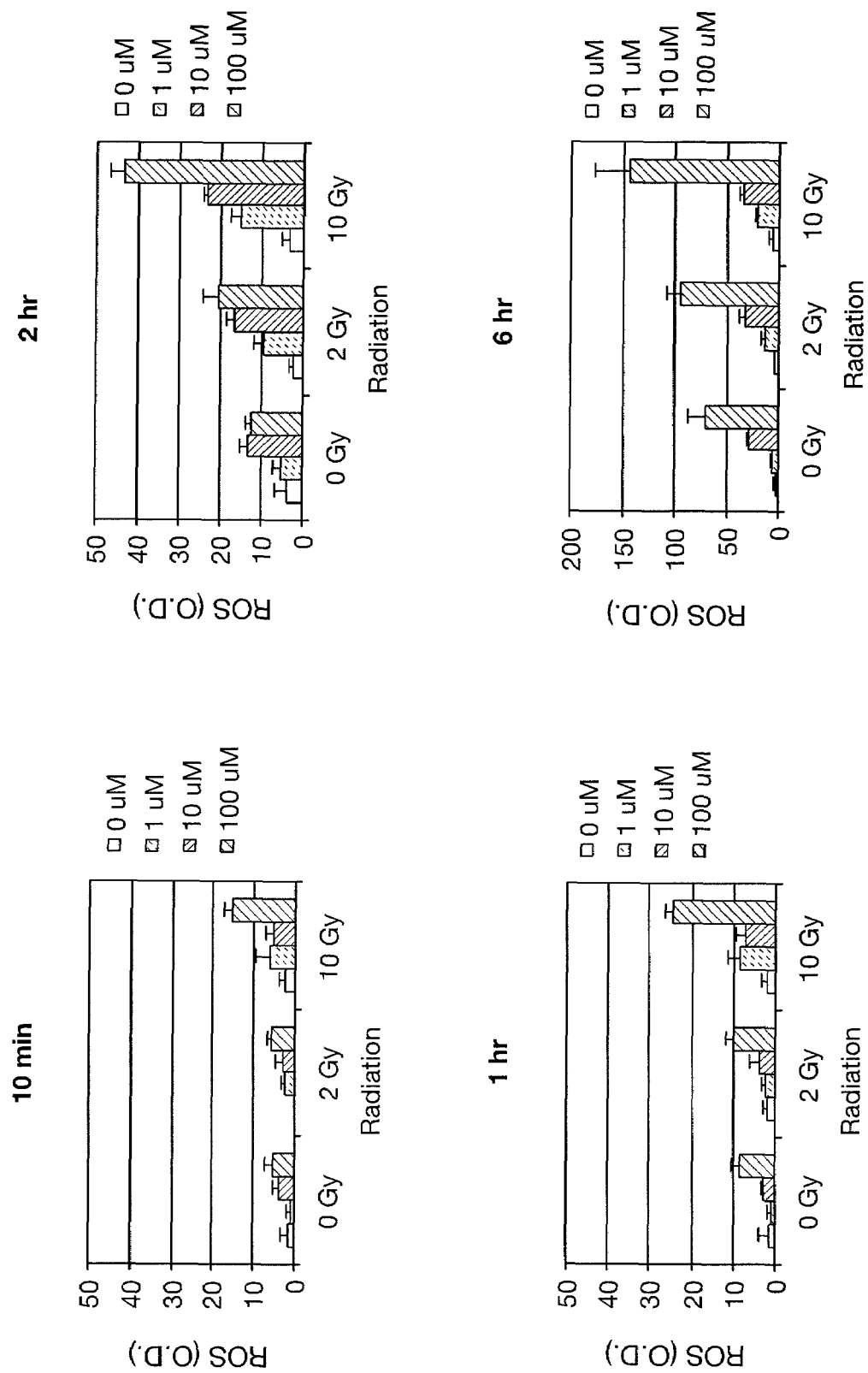
FIG. 2 illustrates ROS production in HT29 tumor cells in the presence of irradiated ABDNAZ.
Figure 3:
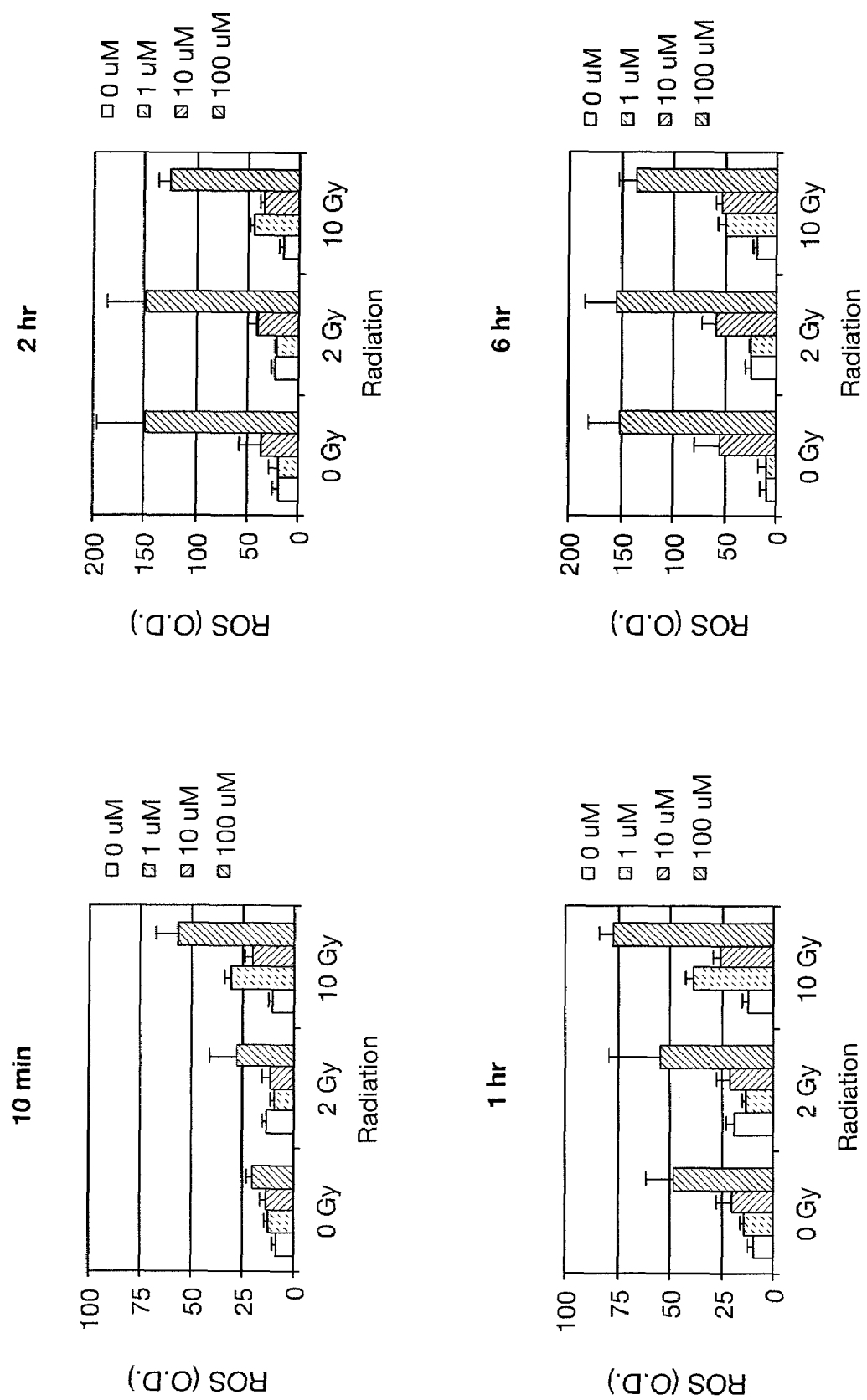
FIG. 3 illustrates ROS production in SCC VII tumor cells in the presence of irradiated ABDNAZ.

FIGS. 2 and 3 illustrate the ROS production in HT29 cells and SCC VII cells, respectively, treated with ABDNAZ and radiation. Combined treatment of ABDNAZ and radiation synergistically induced intracellular ROS generation in HT29 cells and SCC VII cells, as compared with each modality alone.

Example 2

Inhibition of Proliferation of HL60 Cells By ABDNAZ

Figure 4:
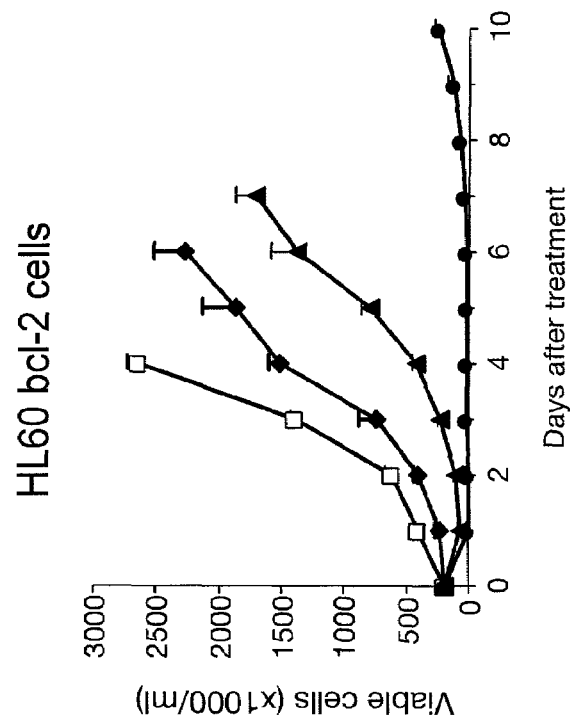
FIG. 4 illustrates inhibition of proliferation of bc1-2 and vector transfected HL60 cells by ABDNAZ.
Figure 4:
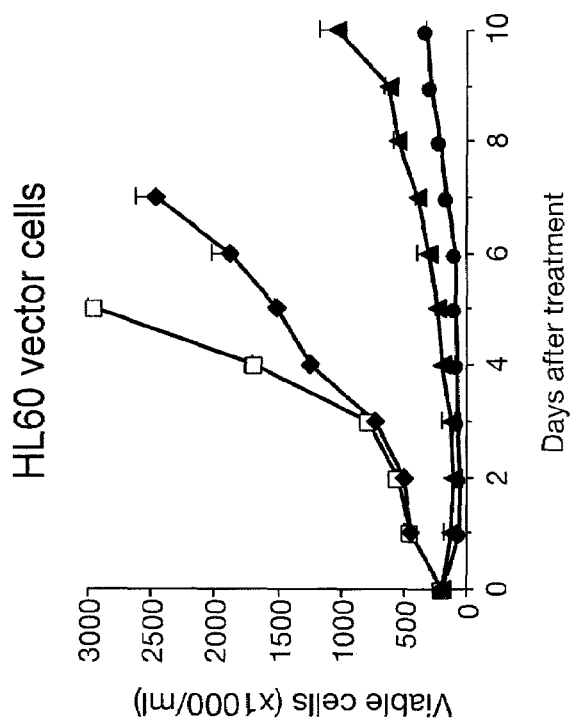

The HL60 cell line, which is an acute promyelocytic leukemia cell line, was stably transfected with bcl-2 oncogene (HL60 bcl-2 cells). The HL60 neo cells were used as a control (HL60 neo). Cells were grown in RPMI1640 media in the presence of ABDNAZ at a concentration of 1 µM, 2 µM or 5 µM. The number of viable cells was counted daily for ten days. The cell growth curves are shown in FIG. 4, which demonstrates that ABDNAZ inhibited cell growth in a dose-dependent manner. A dose of 5 µM of ABDNAZ inhibited cell growth by >95% and HL60 bcl-2 cells were as sensitive as neo cells to ABDNAZ.

Example 3

Induction of Apoptosis of HL60 Cells By ABDNAZ

Figure 5:
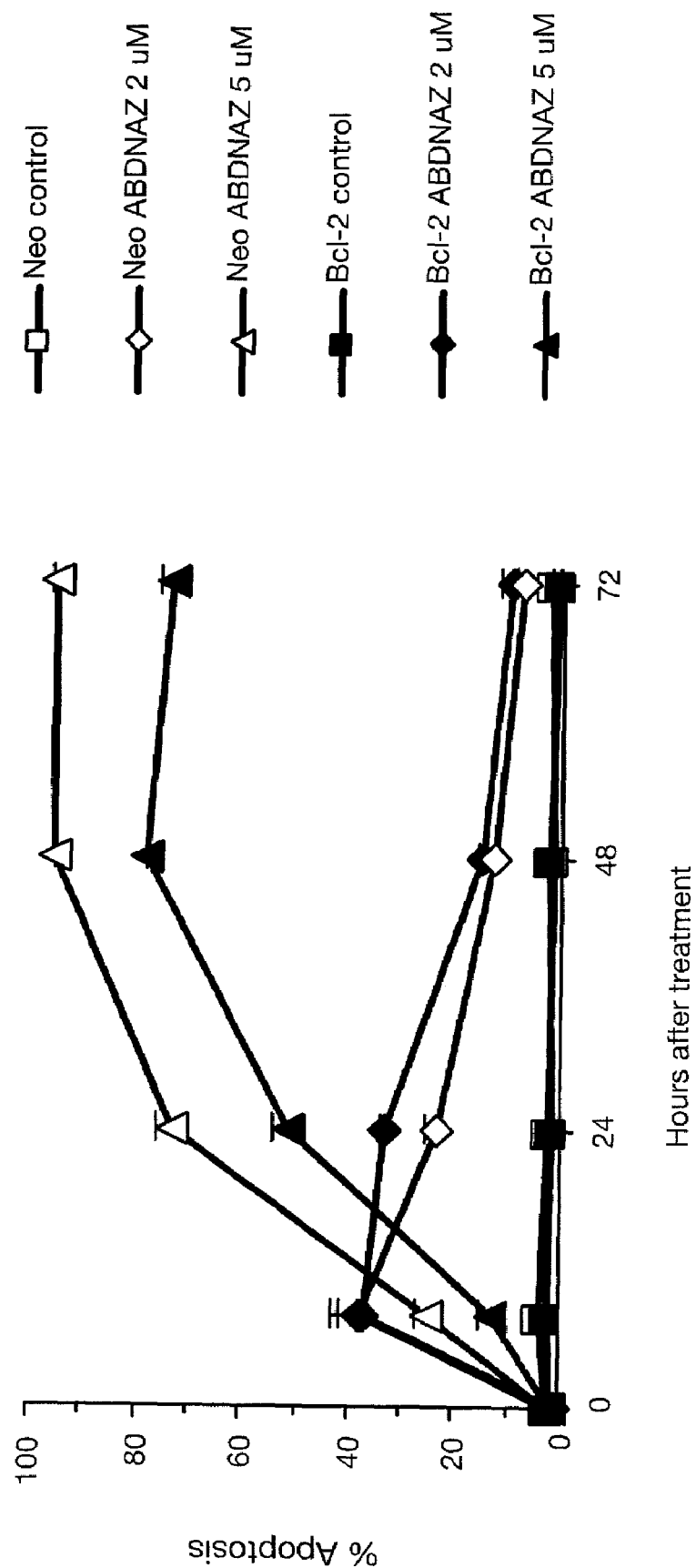
FIG. 5 illustrates induction of apoptosis of bc1-2 and vector transfected HL60 cells by ABDNAZ.
Figure 6:
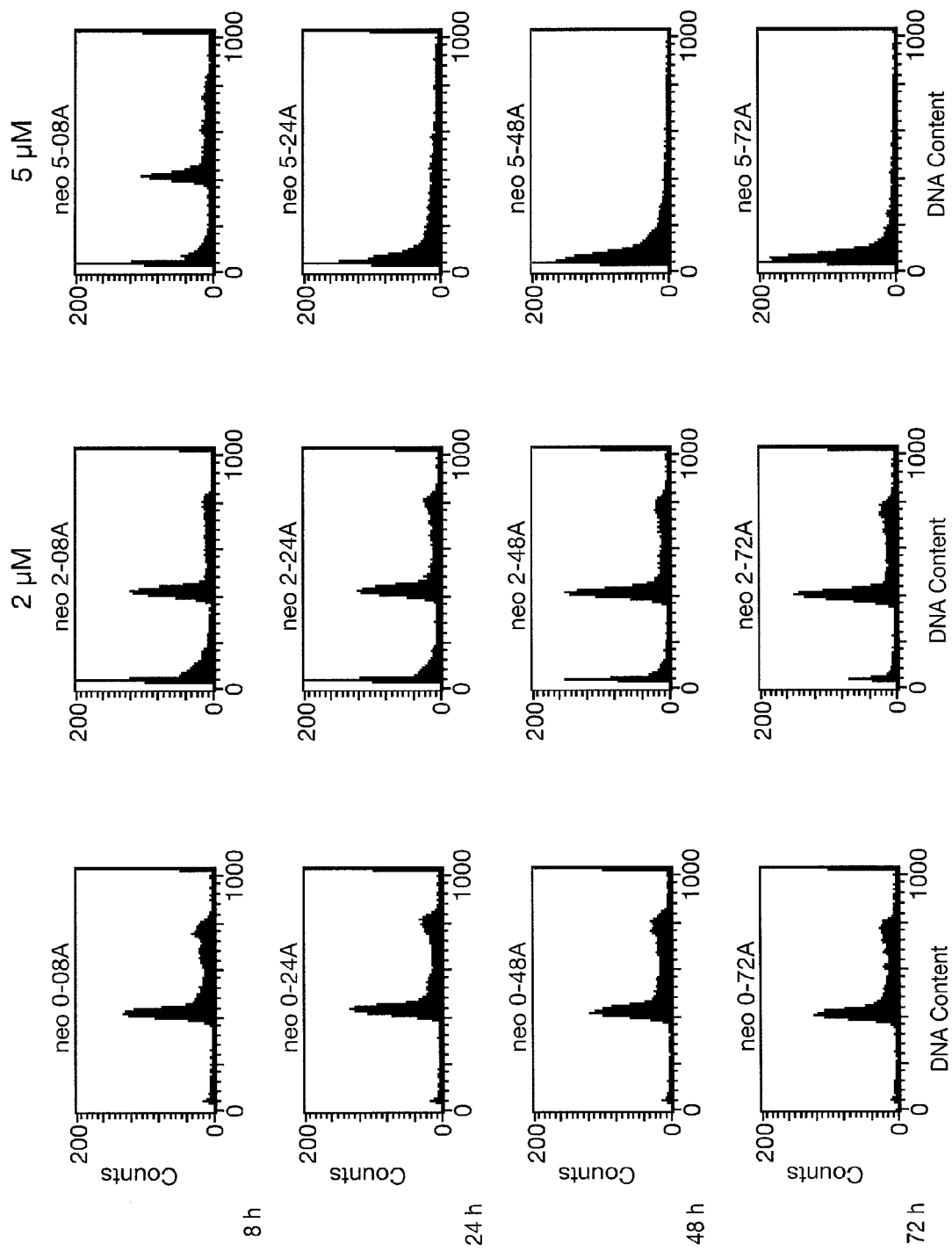
FIG. 6 illustrates the apoptosis and cell cycle profile of HL60 neo cells after exposure to ABDNAZ.
Figure 7:
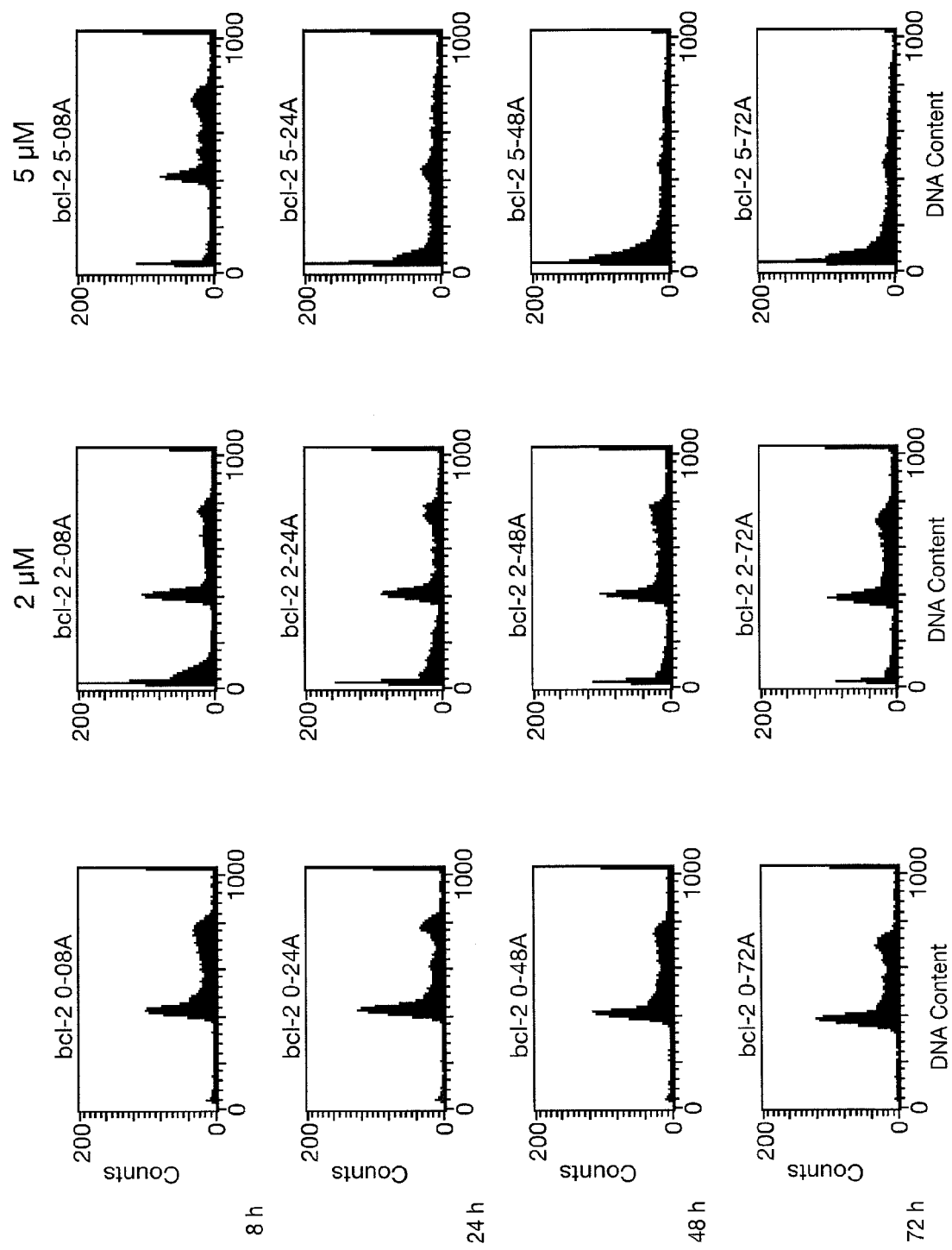
FIG. 7 illustrates the apoptosis and cell cycle profile of HL60 bc1-2 cells after exposure to ABDNAZ.

Cells, prepared and grown as described in Example 2, supra, were collected at 8, 24, 48, and 72 hours after addition of ABDNAZ, and analyzed using FACS. FIG. 5 illustrates the percent of apoptosis vs. time in the presence of ABDNAZ. As can be seen in FIGS. 5, 6 and 7, ABDNAZ induced a very high level of apoptotic cell death in both HL60 neo and bcl-2 cells in a dose-dependent manner. ABDNAZ at 5 µM induced 95% and 78% apoptosis at 48 hours for neo and bcl-2 cells, respectively. At 2 µM, ABDNAZ produced apoptotic cell death that was very similar in HL60 neo and bcl-2 cells with peaks of ~40% at 8 hours. FIGS. 6 and 7 illustrate the detailed histograms of FACS analysis for HL60 neo cells and HL60 bcl-2 cells, respectively.

Example 4

Inhibition of bcl-2 Oncogene Expression by ABDNAZ

Figure 8:
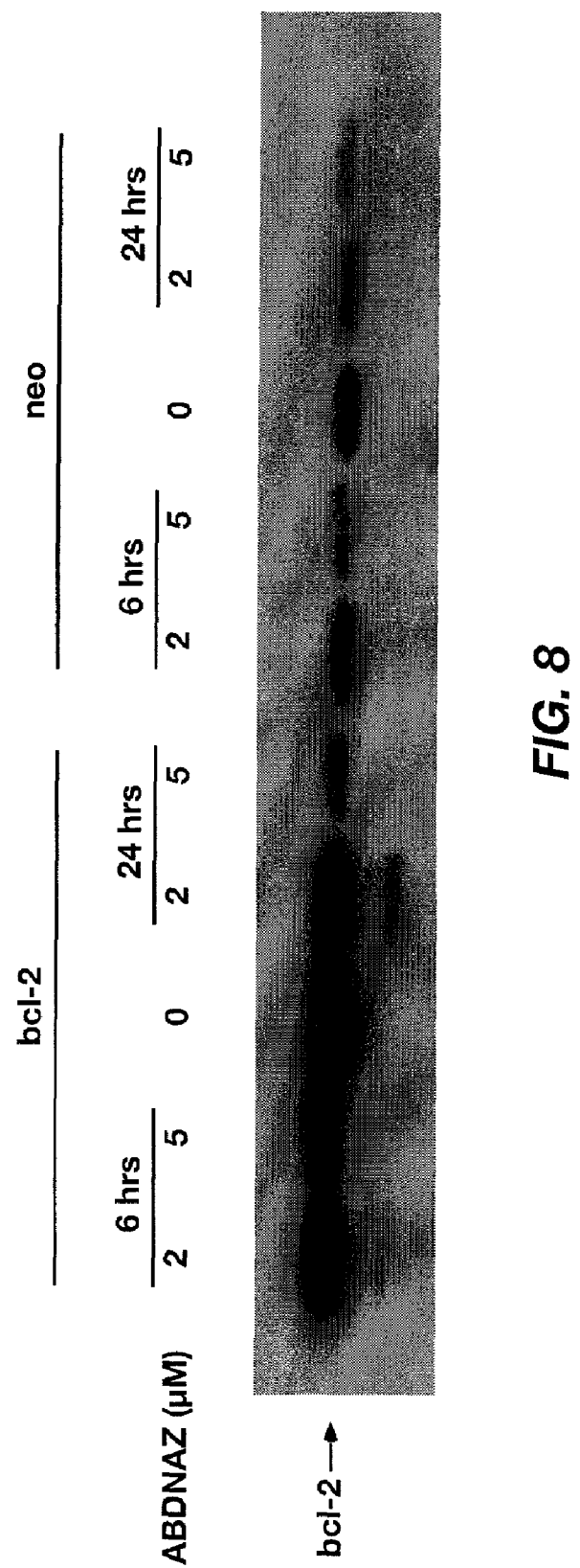
FIG. 8 illustrates the inhibition of bc1-2 expression in HL60 cells.

HL60 cells were treated as described in Example 2, supra. Cells were collected at 6 and 24 hours for Western blot analysis. As shown in FIG. 8, ABDNAZ at 2 and 5 µM inhibited bcl-2 protein expression in both neo and bcl-2 cells in a dose-dependent manner. The bcl-2 protein in HL60 bcl-2-transfected cells may be cleaved in the presence of 2 µM ABDNAZ as indicated by the presence of the lower molecular weight bands after both 6 and 24 hours.

Example 5

Synthesis of ABDNAZ

A 25 ml, three-neck, round-bottomed flask was charged with 7 ml of methylene chloride and 2.50 g (12.3 mmol) of t-BuDNAZ prepared as described in Archibald et al., *Journal of Organic Chemistry,* 1990, 2920. Under nitrogen, 0.16 ml (1.23 mmol) of boron trifluoride etherate was added. After stirring 5 minutes at ambient temperature, 0.54 ml (6.15 mol) of bromoacetyl bromide was added. The solution was heated between 50-60° C. for 2 hours. The darkened reaction mixture was cooled to ambient temperature, diluted with 50 ml methylene chloride, and filtered. The solid was identified as the HBr salt of t-BuDNAZ. The methylene chloride filtrate was washed with two 20 ml portions of water, dried over sodium sulfate, filtered, and evaporated under reduced pressure. The resultant solid was washed with three 20 ml portions of ethyl ether and dried under vacuum to yield 1.24 g (75.2% based on bromoacetyl bromide) of BrADNAZ as a white solid (mp=124-125° C.). $^1$H NMR (CDCl$_3$): δ 3.76 (s, 2H), 4.88 (br s, 2H), 5.14 (br s, 2H); $^{13}$C NMR (CDCl$_3$): δ 165.2, 105.0, 59.72, 57.79, 23.90. Calc. for $C_5H_6BrN_3O_5$: % C 22.41, % H 2.26, % N 15.68; Found: % C 22.61, % H 2.36, % N 15.58. HPLC/MS C-8 reverse phase column with acetonitrile/water mobile phase—m/e 266.95 (100%), 268.95 (98.3%). FTIR: 3014.24 (weak), 1677.66, 1586.30, 1567.65, 1445.55 (NO$_2$), 1367.80, 1338.00, 1251.27 cm$^{-1}$.

Example 6

Synthesis of N-(chloroacetyl)-3,3-dinitroazetidine (ClADNAZ)

A 25 ml, three-neck, round-bottomed flask was charged with 7 ml of methylene chloride and 2.50 g (12.3 mmol) of t-BuDNAZ. Under nitrogen, 0.16 ml (1.23 mmol) of boron trifluoride etherate was added. After stirring 5 minutes at ambient temperature, 0.54 ml (6.15 mol) of chloroacetyl chloride was added. The solution was heated between 50-60° C. for 2 hours. The darkened reaction mixture was cooled to ambient temperature, diluted with 50 ml methylene chloride and filtered. The solid was identified as the HCl salt of t-BuDNAZ. The methylene chloride filtrate was washed with two 20 ml portions of water, dried over sodium sulfate, filtered, and evaporated under reduced pressure. The resultant solid was washed with three 20 ml portions of ethyl ether and dried under vacuum to afford a white solid (mp: 130-132° C.) in 60% yield. CHN for $C_5H_6ClN_3O_5$: Found C: 26.94%, H: 2.53%, N: 17.77%; Calculated C: 26.86%, H: 2.71%, N: 18.79%. FTIR: 2979 (weak), 1690.01, 1577.57, 1438.91 ($NO_2$), 1368.21, 1338.99, 1286.21 $cm^{-1}$. $^1H$ NMR: (DMSO-$d_6$), δ 5.09(2H), 4.81(2H), 3.77(2H). $^{13}C$ NMR: (DMSO-$d_6$), δ 168.58, 106.98, 60.39, 50.38. HPLC: >98% pure. Safety Data: ABL Impact: 80 cm; ABL Friction: 800 at 8 ft/sec; TC ESD Unconfined at 50%: 1.10 Joules (mass ignition on bulk test). DSC Onset: 259.56° C.

Example 7

Synthesis of N-Iodoacetyl-3,3-dinitroazetidine (IADNAZ)

A 100 ml, three neck round-bottomed flask was charged with 40 mL of anhydrous acetone and 2.01 g of BrADNAZ under nitrogen. 1.4 g $K_2CO_3$ was added followed by the addition of 1.2 g sodium iodide. The reaction mixture was allowed to reflux overnight and monitored by proton NMR. The darkened solution was diluted with methylene chloride, the solid was filtered and the filtrate was extracted with 2× 30 mL portions of methylene chloride and water. The organic layer was dried over sodium sulfate and concentrated under vacuum. The solid was purified by flash column chromatography (10% ethyl acetate/hexanes) to yield a white solid (mp 97-100° C.) in 80% yield. Analysis for $C_5H_6IN_3O_5$: Found C: 19.67%, H: 1.80%, N: 12.70%. Calculated C: 19.06%, H: 1.92%, N: 13.24%. FTIR: 2980 (weak), 1667.44, 1568.49, 1439.74 ($NO_2$), 1373.69, 1335.60, 1305.35 $cm^{-1}$. $^1H$ NMR: (DMSO-$d_6$), δ 5.09(2H), 4.81(2H), 3.77(2H). $^{13}C$ NMR: (DMSO-$d_6$), δ 168.58, 106.98, 60.39, 50.38. HPLC: >98% pure. Safety Data: ABL Impact: 80 cm; ABL Friction: 800 at 8 ft/sec; TC ESD, Unconfined 50% 7.30 Joules (no mass ignition on bulk test); SBAT Onset: 286° F. DSC Onset: 253.52° C.

Example 8

Synthesis of N-Azidoacetyl-3,3-dinitroazetidine (AzADNAZ)

A 100 ml, three-neck flask was charged with 40 mL of anhydrous acetone and 2.01 g of BrADNAZ under nitrogen. 1.05 g $K_2CO_3$ was added followed by the addition of 0.4 g sodium azide. The reaction mixture was allowed to reflux overnight and monitored by proton NMR. The darkened solution was diluted with methylene chloride and the solid was filtered. The filtrate was extracted with two 30 mL portions of methylene chloride and water. The organic layer was dried over sodium sulfate and concentrated under vacuum. The solid was purified by flash column chromatography (10% ethyl acetate/hexanes) to yield a white solid (mp 103-104° C.) in 80% yield. Analysis for $C_5H_6N_6O_5$: Found C: 26.84%, H: 2.70%, N: 35.49%. Calculated C: 26.09%, H: 2.63%, N: 34.76%. FTIR: 2981.60 (weak), 2109.15 (strong), 1678.88, 1598.80, 1571.47, 1463.18 ($NO_2$), 1446.89, 1332.20, 1275.28 $cm^{-1}$. $^1H$ NMR: (DMSO-$d_6$), δ 5.08(2H), 4.83(2H), 4.02(2H). $^{13}C$ NMR: (DMSO-$d_6$), δ 169.098, 107.74, 59.84, 58.16. HPLC: >99.7% pure. Safety Data: ABL Impact: 64 cm; ABL Friction: 800 at 8 ft/sec; TC ESD, Unconfined 50% <0.5 Joules (no mass ignition on bulk test); SBAT Onset: 314° F.

Example 9

Synthesis of N-Succinyl-3,3-Dinitroazetidine

A 100 ml, three-neck, round-bottomed flask was charged with 30 mL of anhydrous dichloromethane and 5.0 grams of tert-butyl-3,3-dinitroazetidine (t-BuDNAZ) under nitrogen. 4.5 grams of succinyl chloride was added followed by the addition of 0.5 mL of boron trifluoride etherate. The reaction mixture was heated to 50° C. and monitored by NMR. The reaction mixture was poured slowly into ice and then filtered. The brown solid was washed with 3× 20 mL portions of dichloromethane, dried with sodium sulfate and concentrated under vacuum. The solid was purified by flash column chromatography (10% ethyl acetate/hexanes) to yield a pale white solid in 20% yield (mp: 190-192° C.). Analysis for $C_7H_9N_3O_7$: Found C: 33.93%, H: 3.63%, N: 19%. Calculated C: 34.02%; H: 3.67%; N: 17.00. FTIR: 3004.44 (weak), 1644.78 (strong), 1558.45, 1472.60, 1450.06, 1423.01, 1369.90, 1338.05, 1310.05, 1260.99 $cm^{-1}$. $^1H$ NMR: (DMSO-$d_6$), δ 5.27(2H), 4.85(2H), 2.03(4H). HPLC: >97%. Safety Data: ABL Impact: 64 cm; ABL Friction: 800 at 8 ft/sec; TC ESD, Unconfined at 50%<0.26 Joules (no mass ignition at 8 Joules). DSC Onset: 253.86° C.

Example 10

Synthesis of N-Fumaryl-3,3-Dinitroazetidine

A 100 ml, three-neck, round-bottomed flask was charged with 8.69 grams of tert-butyl-3,3-dinitroazetidine (t-BuDNAZ) under nitrogen and 5 mL of furmaryl chloride was added followed by the addition of 0.5 mL of boron trifluoride etherate at 0° C. for 2 hours. The reaction mixture was monitored by NMR. The thick paste was washed with methanol and then poured into ice water. The solid was filtered and washed with 200 mL of water and dried under vacuum, which afforded a pale yellow solid in 20% yield (mp: 240° C.). Analysis for $C_7H_7N_3O_7$: Found C: 34.9%, H: 3.2%, N: 19.6%. Calculated C: 34.3%; H: 2.9%; N: 17.1. FTIR: 3082.73 (weak), 1664.79 (strong), 1577.69, 1430.19 ($NO_2$), 1366.92, 1274.30, 1231.24, 1213.45 $cm^{-1}$. $^1H$ NMR: (DMSO-$d_6$), δ 5.88(2H), 5.29(2H), 4.90(2H). HPLC: >96%. Safety Data: ABL Friction: 800 at 8 ft/sec, TC ESD Unconfined at 50%: 1.05 Joules (mass ignition on bulk test).

Example 11

Synthesis of N-Trifluromethyl-3,3-Dinitroazetidine

A 100 ml, three-neck round-bottomed flask was charged with 2.28 grams of tert-butyl-3,3-dinitroazetidine (t-BuDNAZ) under nitrogen. 10 mL of trifluoroacetic anhydride was added followed by the addition of 0.3 mL of boron trifluoride etherate. The reaction mixture was heated to 50° C. and monitored by NMR. The reaction was concentrated under vacuum. The residual oil was washed with water. The residual oil was added to hot hexanes and to afford 460 mg of white needles (mp: 70-71° C.). Analysis for $C_5H_4F_3N_3O_5$: Found C: H:, N: Calculated C: 24.70%, H: 1.66%, N: 17.29%. FTIR: 2991 (weak), 1716, 1683.96, 1591.37, 1576.43 ($NO_2$), 1165.92, 1134.12 $cm^{-1}$. $^1H$ NMR: (DMSO-$d_6$), δ 5.39(2H), 5.04(2H). HPLC: >96% pure. Safety Data: ABL Friction: 800 at 8 ft/sec; TC ESD Unconfined at 50%: >8 Joules. DSC Onset: 240.75° C.

Finally, it should be noted that there are alternative ways of implementing the present invention. Accordingly, the present embodiments are to be considered as illustrative and not restrictive, and the invention is not to be limited to the details given herein, but may be modified within the scope and equivalents of the appended claims. All publications and patents cited herein are incorporated by reference.

All references and publications cited herein are incorporated by reference in their entirety.

What is claimed is:

1. A method of synthesizing a N-(haloacetyl)-3,3-dinitroazetidine compound, comprising:
   reacting tert-butyl-3,3-dinitroazetidine ("t-BuDNAZ"), an acid catalyst, and a haloacetyl halide.

2. The method of claim 1, wherein reacting t-BuDNAZ, an acid catalyst, and a haloacetyl halide comprises reacting 2 molar equivalents of t-BuDNAZ, 1 molar equivalent of the haloacetyl halide, and the acid catalyst.

3. The method of claim 1, wherein reacting t-BuDNAZ, an acid catalyst, and a haloacetyl halide comprises reacting t-BuDNAZ, the haloacetyl halide, and the acid catalyst in methylene chloride.

4. The method of claim 1, wherein reacting t-BuDNAZ, an acid catalyst, and a haloacetyl halide comprises reacting t-BuDNAZ, boron trifluoride etherate, and bromoacetyl bromide.

5. The method of claim 4, wherein reacting t-BuDNAZ, boron trifluoride etherate, and bromoacetyl bromide comprises producing N-(bromoacetyl)-3,3-dinitroazetidine at a yield of 75.2%.

6. The method of claim 4, further comprising filtering, washing, and drying a reaction product of t-BuDNAZ, boron trifluoride etherate, and bromoacetyl bromide to produce N-(bromoacetyl)-3,3-dinitroazetidine.

7. The method of claim 6, further comprising reacting the N-(bromoacetyl)-3,3-dinitroazetidine, sodium iodide, and a base.

8. The method of claim 7, further comprising filtering, washing, and drying a reaction product of N-(bromoacetyl)-3,3-dinitroazetidine, sodium iodide, and the base to produce N-(iodoacetyl)-3,3-dinitroazetidine.

9. The method of claim 6, further comprising reacting the N-(bromoacetyl)-3,3-dinitroazetidine, sodium azide, and a base.

10. The method of claim 9, further comprising filtering, washing, and drying a reaction product of N-(bromoacetyl)-3,3-dinitroazetidine, sodium azide, and the base to produce N-(azidoacetyl)-3,3-dinitroazetidine.

11. The method of claim 1, wherein reacting t-BuDNAZ, an acid catalyst, and a haloacetyl halide comprises reacting t-BuDNAZ, boron trifluoride etherate, and chloroacetyl chloride.

12. The method of claim 11, wherein reacting t-BuDNAZ, boron trifluoride etherate, and chloroacetyl chloride comprises producing N-(chloroacetyl)-3,3-dinitroazetidine at a yield of 60%.

13. The method of claim 11, further comprising filtering, washing, and drying a reaction product of t-BuDNAZ, boron trifluoride etherate, and chloroacetyl chloride to produce N-(chloroacetyl)-3,3-dinitroazetidine.

14. A method of synthesizing a N-(haloacetyl)-3,3-dinitroazetidine compound, comprising:
   reacting tert-butyl-3,3-dinitroazetidine ("t-BuDNAZ"), an acid catalyst, and a haloacetyl halide selected from the group consisting of bromoacetyl bromide and chloroacetyl chloride.

* * * * *